United States Patent [19]
Davies

[11] Patent Number: 6,065,356
[45] Date of Patent: May 23, 2000

[54] MONITORING CHARACTERISTICS OF FLOWING PARTICULATE MATERIAL

[75] Inventor: Clive Eric Davies, Lower Hutt, New Zealand

[73] Assignee: Industrial Research Limited, NZX

[21] Appl. No.: 09/194,331

[22] PCT Filed: May 30, 1997

[86] PCT No.: PCT/NZ97/00069

§ 371 Date: May 26, 1999

§ 102(e) Date: May 26, 1999

[87] PCT Pub. No.: WO97/45717

PCT Pub. Date: Dec. 4, 1997

[30] Foreign Application Priority Data

May 31, 1996 [NZ] New Zealand .............................. 286717
Nov. 26, 1996 [NZ] New Zealand .............................. 299828

[51] Int. Cl.[7] ..................................................... G01N 15/02
[52] U.S. Cl. ............................................................ 73/865.5
[58] Field of Search ................................. 73/865.9, 865.5, 73/862.541

[56] References Cited

FOREIGN PATENT DOCUMENTS

WO 93/22652  11/1993  WIPO .................................. 73/865.5

*Primary Examiner*—Robert Raevis
*Attorney, Agent, or Firm*—Dann, Dorfman, Herrell and Skillman, P.C.

[57] ABSTRACT

Determining a characteristic or characteristics of a particular material such as the type, constitution, surface characteristics, or general flowability of the material. The material flows through a measuring cell (1) of constant volume so as to maintain a substantially constant volume of flowing material in the measuring cell. The weight of material in the measuring cell is continuously monitored and oscillations in the weight of the contents of the measuring cell as the material flows through the measuring cell are compared with stored comparative information to determine the material.

7 Claims, 8 Drawing Sheets

Figure 7a    Power Spectrum for Wheat

Figure 7b    Power Spectrum for Barley

Figure 8

MONITORING CHARACTERISTICS OF FLOWING PARTICULATE MATERIAL

FIELD OF INVENTION

The invention comprises a method and apparatus for determining characteristics of a flowing particulate material.

BACKGROUND OF INVENTION

There are at least two previous, investigations aimed at utilizing naturally occurring periodic phenomena in powder flow for the characterisation of particulate systems. Budny, Thomas J., Powder Technology, (Lausanne), 23, 197 (1979) used a Table Model Instron to measure the fluctuations in the shear force when a powder bed was sheared. Stick-slip amplitudes were related to the flow rate from a powder dispensing device, but not to general flow properties. Kaye, Brian H., Gratton-Lumatainen, Julie and Neil Faddis, Part. Part. Syst. Charact., (Weinheim), 12, 232 (1995) correlated the avalanching behaviour of a powder contained in a rotating drum with fines content.

SUMMARY OF INVENTION

The present invention provides an improved or at least alternative method and apparatus for determining characteristics of a flowing particulate material.

In broad terms in one aspect the invention comprises a method for determining a characteristic or monitoring characteristics of a particulate material, comprising:

causing the material to flow through a measuring cell of constant volume so as to maintain a substantially constant volume of flowing material in the measuring cell, and continuously monitoring the weight of material in the measuring cell and comparing oscillations in the weight of the contents of the measuring cell as the material flows through the measuring cell with reference information to determine said characteristic(s) of the flowing material.

Preferably said comparing is carried out by computing means and the reference information comprises stored comparative information in memory.

In broad terms in another aspect the invention comprises apparatus for determining a characteristic or characteristics of a particulate material, comprising:

a measuring cell having an inlet by which material may flow into the measuring cell to maintain a substantially constant volume of flowing material in the measuring cell and an outlet for exit of the flowing material, weighing means associated with the measuring cell for providing a continuous indication of the weight of the contents of the cell, computing means for comparing oscillations in the weight of material in the measuring cell with reference information in memory to determine said characteristic(s) of the flowing material.

Preferably the method comprises determining the type or constitution, surface characteristics, or general flowability of the particulate material by comparing oscillations in the weight of the contents of the measuring cell as the material flows through the measuring cell with said stored comparative information.

Preferably the method comprises determining the proportions of particles of different sizes or of different size ranges by comparing oscillations in the weight of the contents of the weighing cell with said stored comparative information.

Preferably the method comprises determining the proportions of particles of a smaller size relative to a balance of particles of a larger size in the flowing material by comparing to oscillations in the weight of the contents of the weighing cell to stored comparative information.

Preferably the method comprises determining the proportion of one type of material relative to a balance of one or more other types of material in the flowing material by comparing oscillations in the weight of the contents of the weighing cell to stored comparative information.

Preferably the weight fluctuations are analysed to produce frequency spectra or phase space data which is compared with stored data on various material types.

Other characteristics which may be monitored include the homogeneity of the material.

BRIEF DESCRIPTION OF FIGURES

The invention will be further described, by way of example and without intending to be limiting, with reference to the accompanying drawings, where.

DETAILED DESCRIPTION

Figure 1:
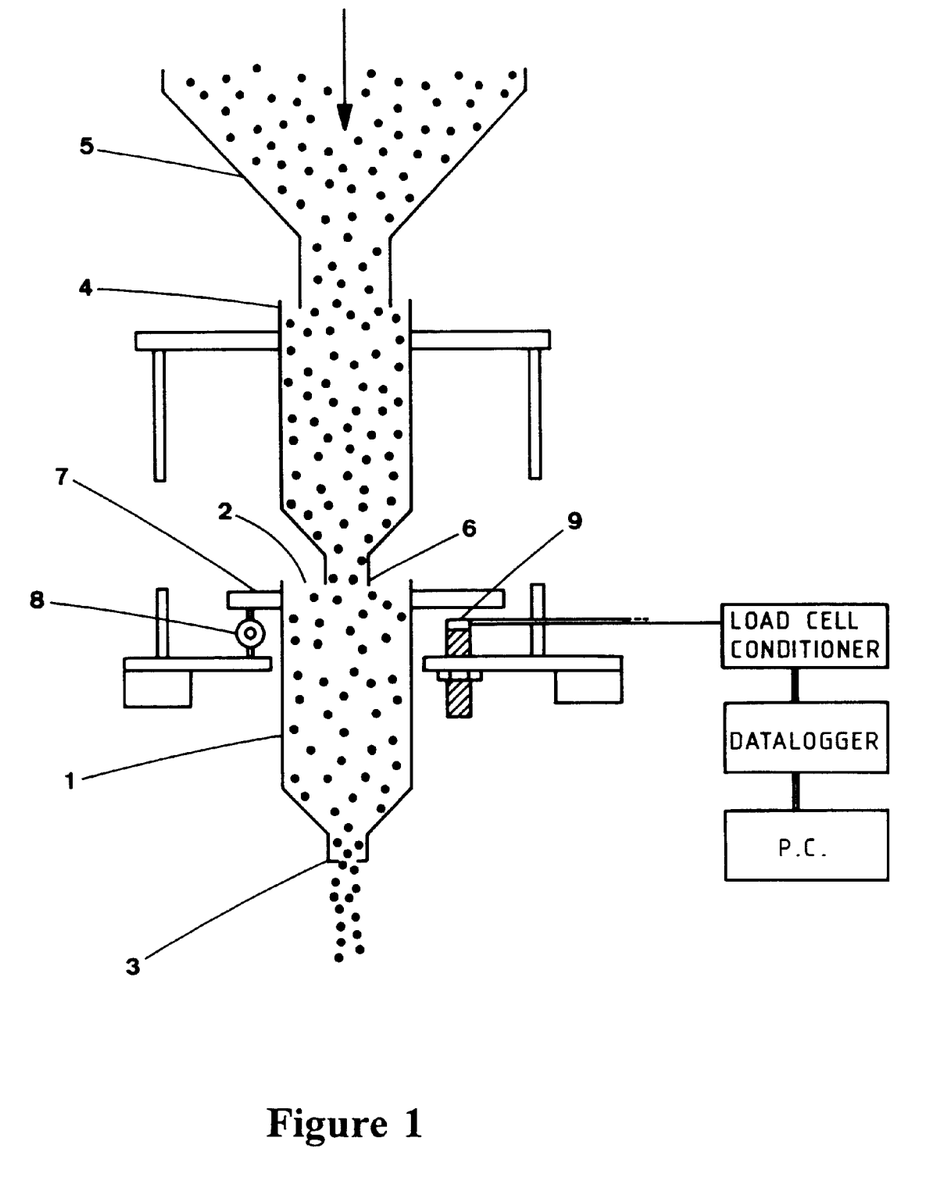
FIG. 1 schematically shows one configuration of apparatus of the invention.

Referring to FIG. 1 the measuring cell 1 of the form of apparatus shown comprises an upstanding tubular cylinder in shape. Other shapes of measuring cell could be employed and the measuring cell need not necessarily be of a regular or symmetrical shape.

The entry to the cylindrical measuring cell 1 is open at the top to provide an inlet 2. In an alternative arrangement the top of the measuring cell could comprise a reverse truncated cone for example, with an inlet orifice sufficiently large to accommodate the flow of material into the measuring cell, but to otherwise prevent unwanted dirt or debris entering the measuring cell. At its other end the measuring cell 1 comprises an outlet 3.

A feed cell 4 is mounted above the measuring cell 1 as shown. In the particular arrangement shown the feed cell 4 is also an upstanding tubular cylinder in shape, and it is mounted above the measuring cell such that the measuring cell and the feed cell are in line with their vertical longitudinal axes coincidental. The feed cell is filled with the particulate material by the material flowing from a storage hopper 5, in turn mounted above the feed cell 4. Particulate material entering the storage hopper 5 from a production stream, for example, will in turn pass into the feed cell.

The feed cell 4 ensures a regular flow through the outlet 6 of the feed cell to the measuring cell 1. The outlet 6 of the feed cell is larger than the outlet 3 of the measuring cell. Material flowing from the feed cell 4 into and through the measuring cell 1 will fill the measuring cell, and the top of the flowing material in the measuring cell at any instant will in general form a cone shape. The angle of repose of the converging sides of the cone of material is relatively constant. It is most preferred that the spacing between the measuring cell 1 and the feed cell 4 and also between the feed cell and the supply hopper, and the relative sizes of the outlet 3 of the measuring cell and the outlet 6 of the feed cell, and also the size of the outlet of the supply hopper 5, are such that the converging sides of the material at the top of the measuring cell meet the outlet 6 of the feed cell, as will the sides of the material at the top of feed cell to the supply hopper outlet, as indicated in FIG. 1. With such an arrangement the measuring cell 1 will contain a substantially constant volume of material flowing through the measuring cell (without necessarily being full to overflowing) and material will flow from the feed cell into the measuring cell as fast as it flows from the measuring cell. In an alternative but less preferred arrangement however, the feed cell could be positioned higher than the measuring cell, so that excess material will spill from the top of the measuring cell, and the apparatus could be contained in a suitable outer casing to catch this excess material and redirect it back. into the material flow beyond the measuring cell.

In the arrangement shown in FIG. 1 a separate supply hopper 5 and feed cell 4 are employed but the supply hopper is not essential and a feed cell alone could be employed without a separate supply hopper as such, with material from a production stream entering the feed cell directly. Alternatively the feed cell could comprise a short conduit extending from the supply hopper outlet as an integral part of the supply hopper.

The measuring cell is supported by means arranged to provide an indication of the weight thereof, which in FIG. 1 is schematically indicated by an arm 7 supported on one side by a pivot bearing 8 and on the other to a load cell 9. Any suitable mechanical arrangement for supporting the measuring cell and any suitable arrangement of load cells, strain gauges, scales or the like which will determine the weight thereof may be employed.

The load cell 9 provides a continuous weight indication of the contents of the measuring cell at any instant. The load cell output is sampled at at least twice the frequency of anticipated weight oscillations (Nyquist), and preferably at 30 samples/second or more, typically by a data logger and/or a microprocessor/PC. Knowing the constant volume of the measuring cell the instantaneous bulk density of the contents of the weighing cell at each sample may be calculated from the weight indication provided (divided by the volume of the measuring cell calibrated under static conditions).

Figure 2A:
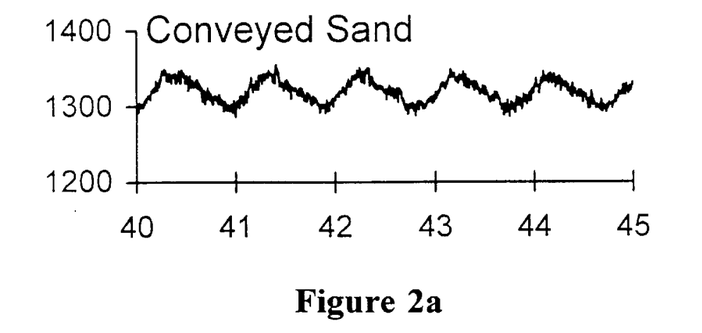
FIGS. 2a, 2b and 2c are plots of fluctuations in bulk density of batches of sand, wheat, and polypropylene pellets flowing through an experimental apparatus, over time.
Figure 2B:
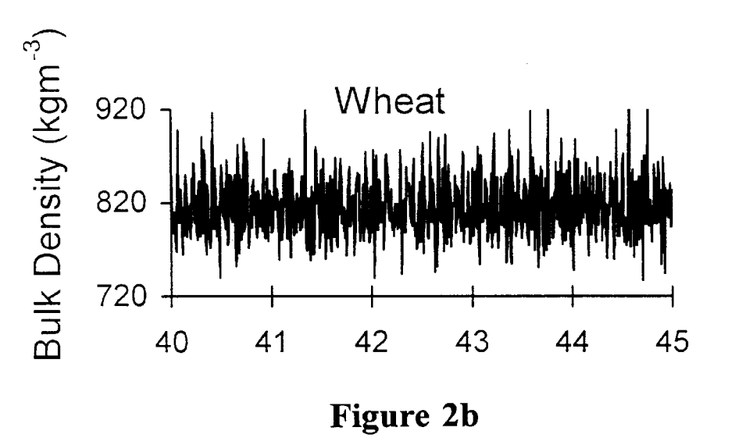
Figure 2C:
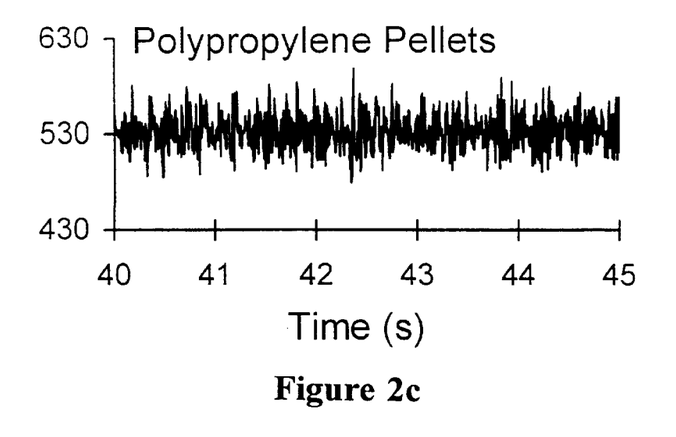

In a first preferred mode of operation, the apparatus of FIG. 1 is used to determine the proportion of particles of a smaller size relative to a balance of particles of a larger size, and in particular the proportion of fines or smaller particles present in the flowing material. FIGS. 2a, 2b and 2c show bulk density variations over time for batches of sand, wheat, and polypropylene pellets as the sand, wheat and pellets flowed through apparatus of the invention of the general type shown in FIG. 1, the sand, wheat and pellets having loose poured bulk densities of about 1318 kg m$^{-3}$, 757 kg m$^{-3}$, and 528 kg m$^{-3}$ respectively. It can be seen that the instantaneous bulk density or weight of the contents of the measuring cell 1 oscillates regularly over time as the material flows through the measuring cell. The magnitude of the oscillations can be characterised by their standard deviation.

Figure 3A:
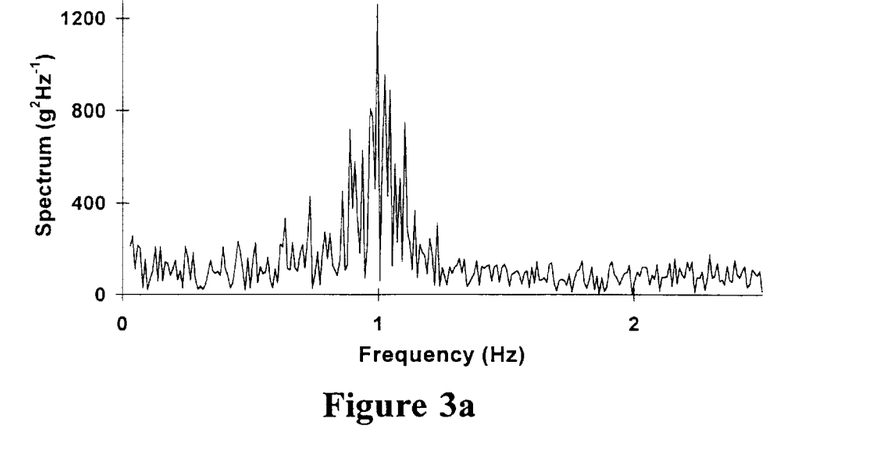
FIGS. 3a, 3b and 3c are plots of the power spectra of the fluctuations in bulk density for the similar sand, wheat, polypropylene pellet batches.
Figure 3B:
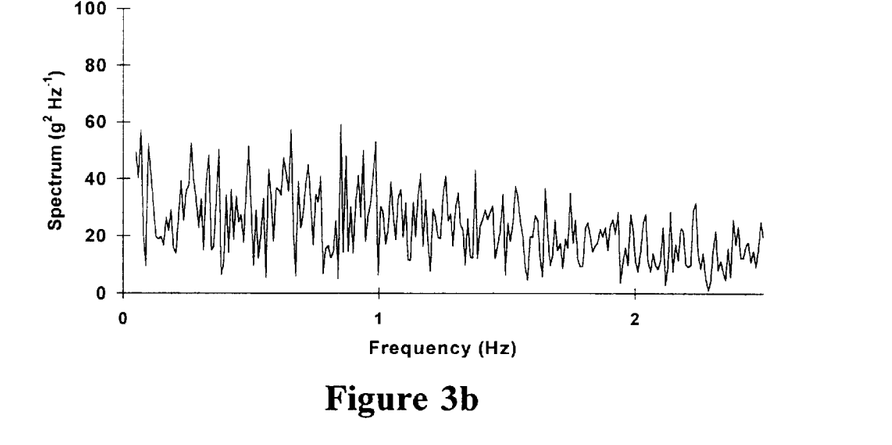
Figure 3C:
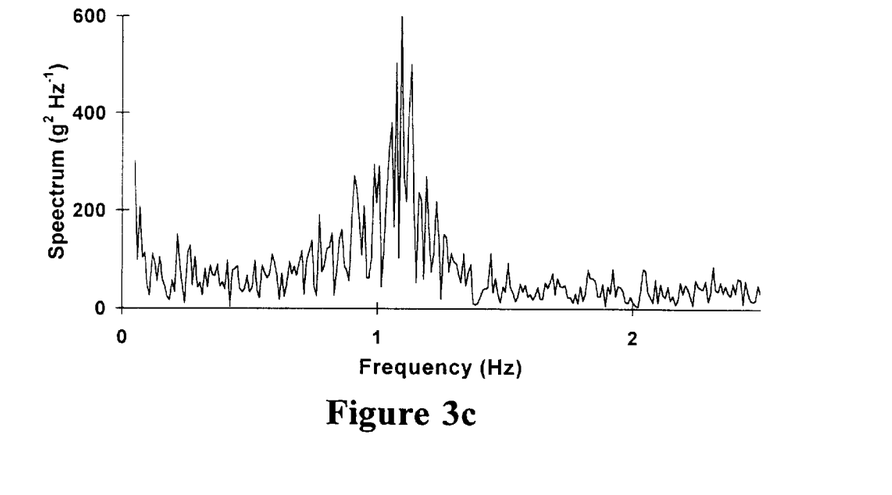

FIGS. 3a, 3b and 3c show the power spectra for each of these samples, obtained by fast Fourier analysis, and it can be seen that in each case there is a characteristic or mean frequency with other frequencies of lesser intensity being distributed on either side of the centre frequency.

Figure 4:
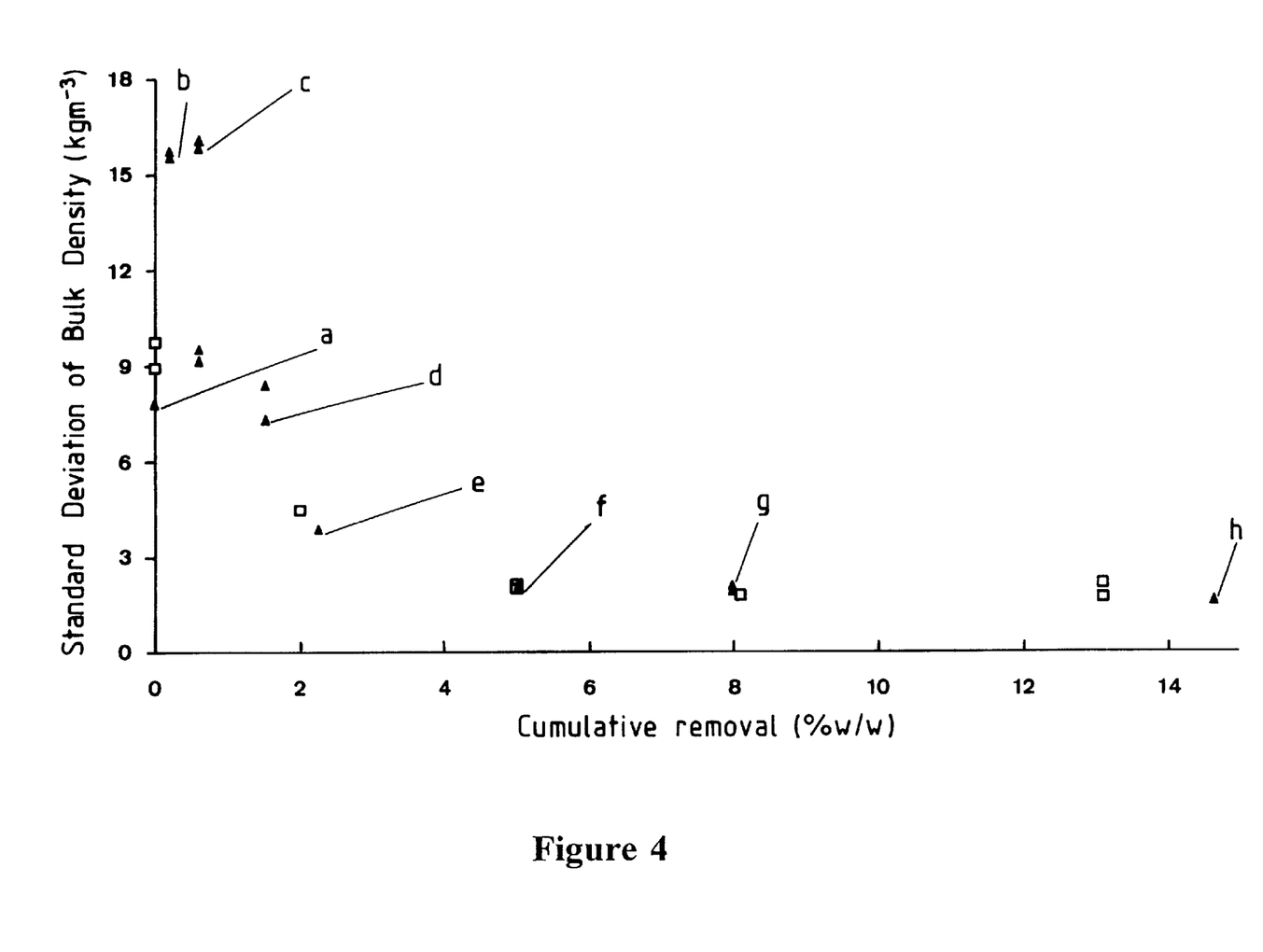
FIG. 4 is a plot of the standard deviation of the measured bulk density for batches of sand a–h with decreasing proportions of fines or particles below a predetermined size relative to the balance of larger particles.

FIG. 4 is a plot of the standard deviation from the mean bulk density for eight batches of sand a–h having an increasingly smaller percentage of fines present, and it can be seen that as the proportion of fines reduces, the standard deviation reduces.

Figure 5A:
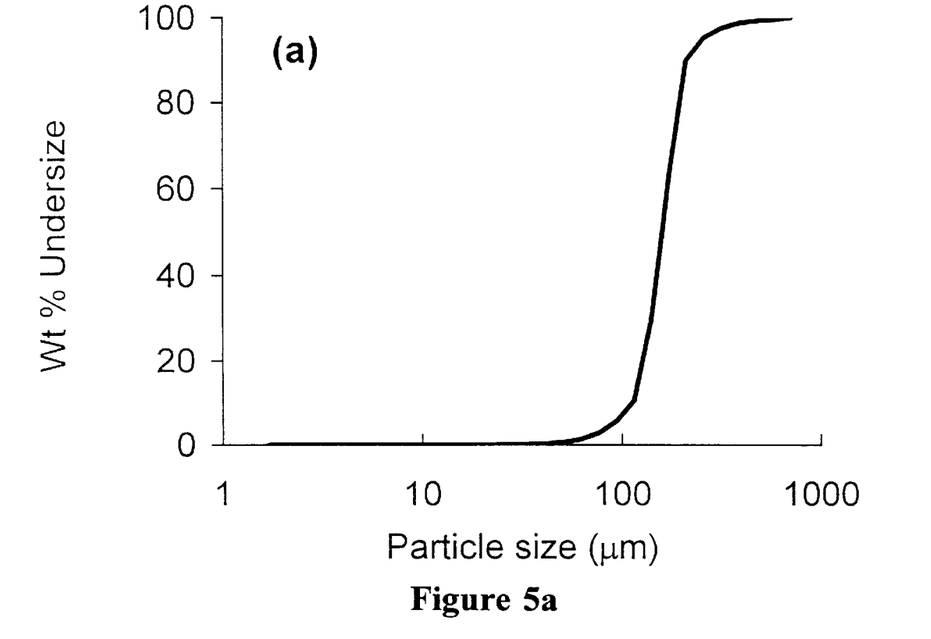
FIGS. 5a and 5b are plots of the size distribution data for the batches of sand a–h.
Figure 5B:
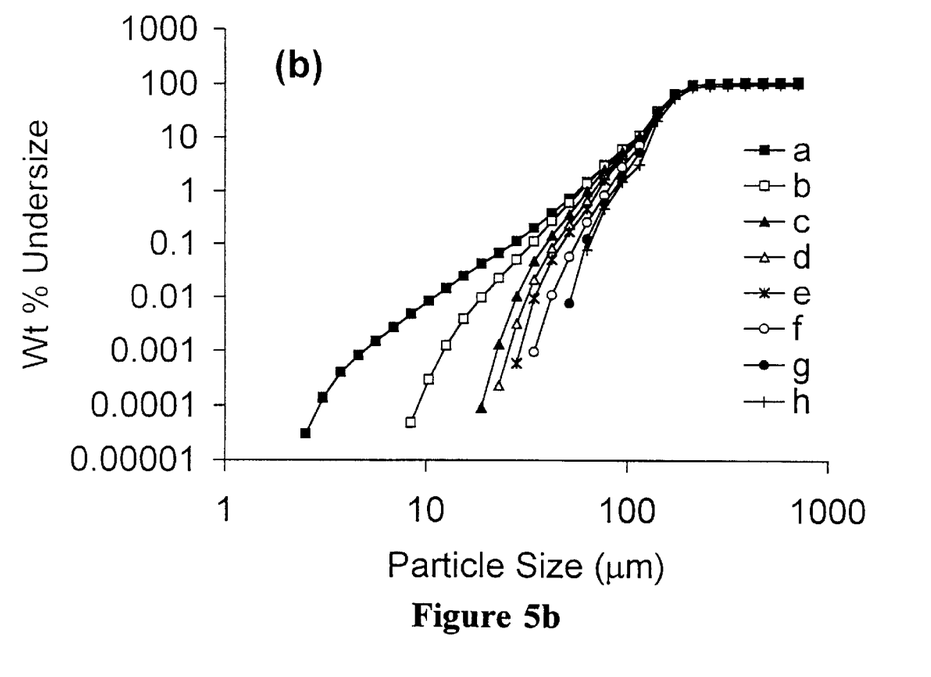

The associated size distribution data for the conveyed sand and also the distributions after each successive passage through a classifier to remove fines for the experiments are shown in FIG. 5. FIG. 5a has been drawn in the conventional manner with the ordinate on a linear scale to satisfy continuity, while in FIG. 5b the ordinate is logarithmic to permit better resolution of the small quantities of the finer sizes.

In the apparatus shown in FIG. 1 the microprocessor is arranged to determine by reference to the standard deviation of the weight or bulk density oscillations, the proportion of fines or smaller particles present in the flowing material, and may be arranged to-determine the proportion of fines less than a predetermined size. As the general flowability of many materials is related to the fines content, the microprocessor may also be arranged to provide an output indicating general flowability. The apparatus may also monitor and indicate changes in homogeneity of the material passing through the apparatus and indicate when there has been any significant change in homogeneity relative to the ideal.

In a second preferred mode of operation, the apparatus of FIG. 1 is used to determine the proportion of one component to a balance of another type of material relative to another component of the flowing material. The material types may be wheat and barley for example, or particles of similar size but different surface characteristics, for example.

Figure 6A:
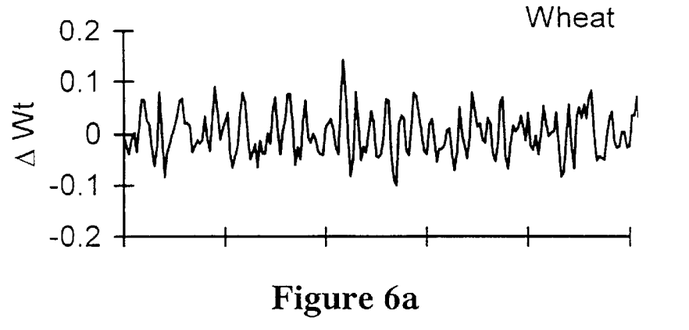
FIGS. 6a, 6b and 6c are plots of the percent deviation of weight fluctuations for wheat, cleaned wheat and barley.
Figure 6B:
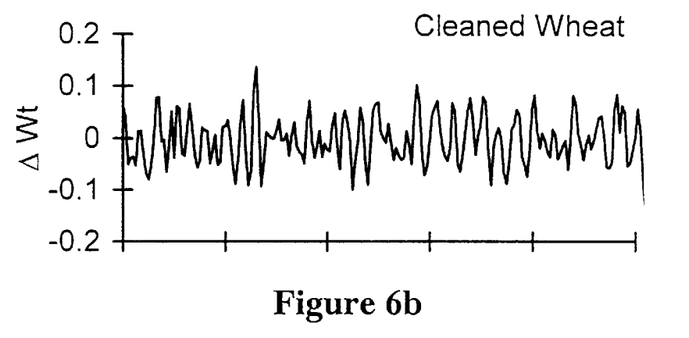
Figure 6C:
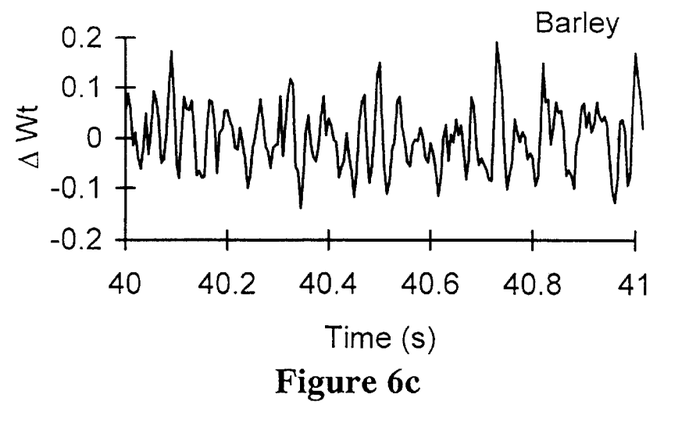

It has been determined that changes in particle properties and size distribution are associated with differences in the structure of the oscillating component of the weight signal from the load cell 9. FIGS. 6a, 6b and 6c show one second portions of the percentage deviation from the mean weight over time ($\Delta Wt$) of the fluctuating weight signal for wheat containing chaff (4–5%), cleaned wheat and barley.

Figure 7A:
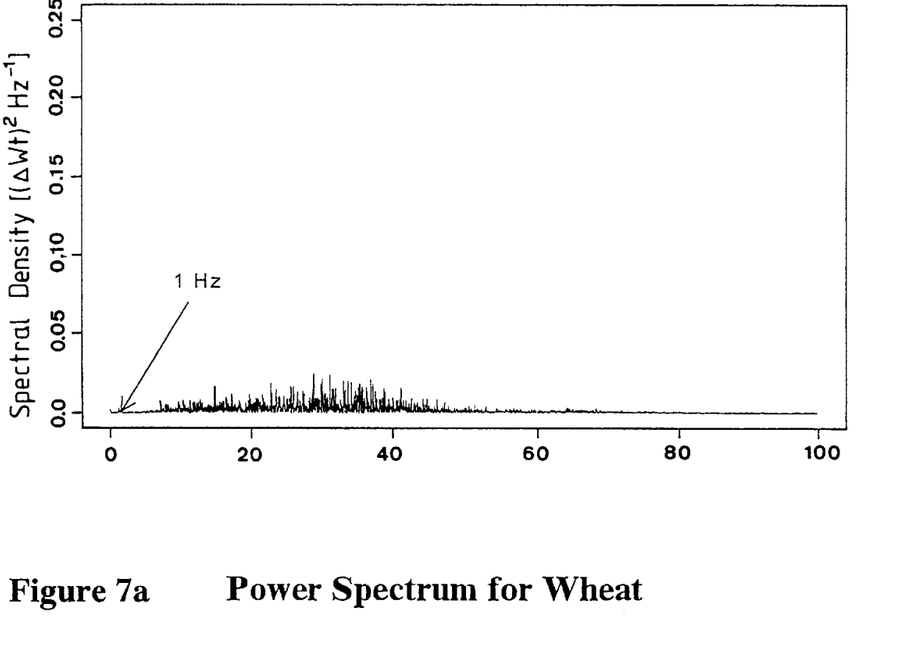
FIGS. 7a and 7b are plots of the power spectra of the deviation of weight fluctuations for wheat and barley.
Figure 7B:
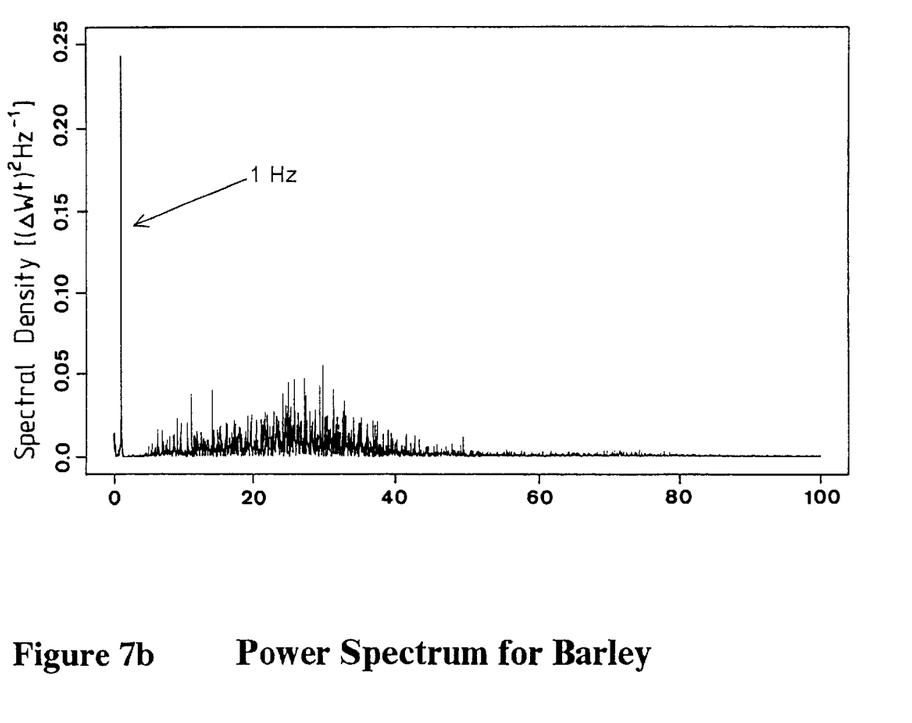

FIGS. 7a and 7b show the power spectra for these wheat and barley signals. It can be seen that while the time series plots appear similar, the frequency distribution obtained by fourier analysis of these series reveals a distinctive power spectra density for each type of material. This can be further enhanced by appropriate filtering of the signal.

Figure 8:
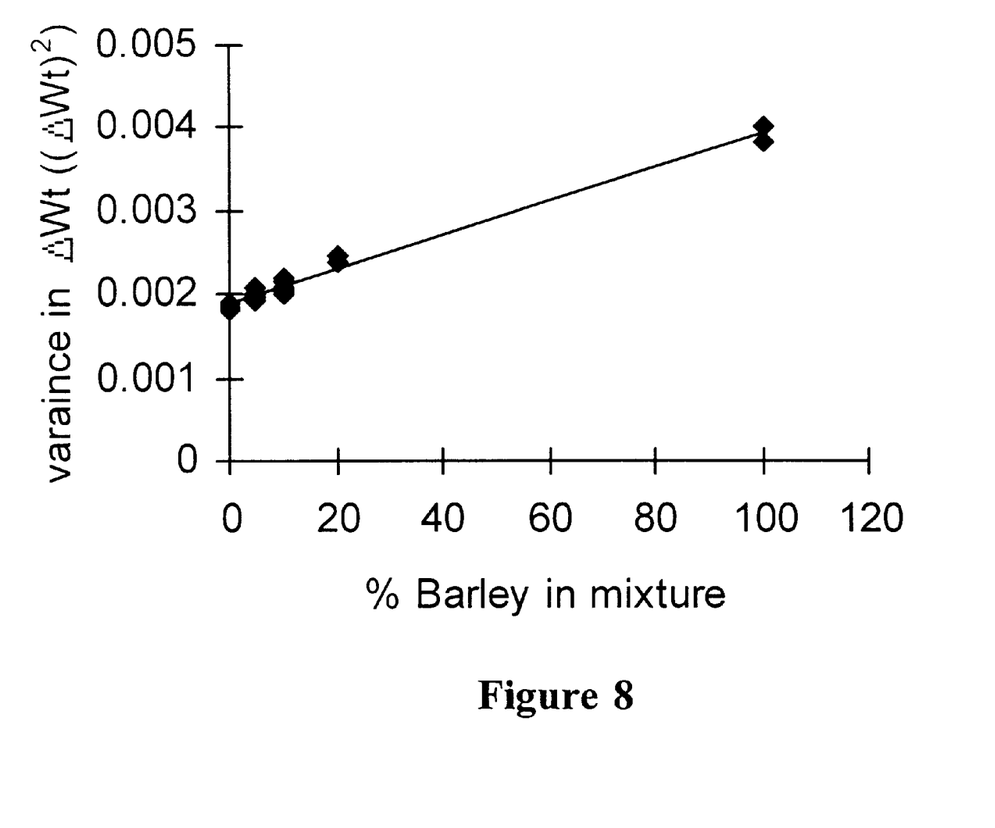
FIG. 8 is a plot of the variance in the deviation of weight fluctuations for wheat/barley mixtures.

FIG. 8 shows the variance in $\Delta Wt$ of the fluctuating weight signal for wheat/barley mixtures. It can be seen that as the percentage of barley in the mixture increases, so does the variance in $\Delta Wt$.

Table 7 lists the mean weights in the measuring vessel and the variances obtained in 10 consecutive experiments with wheat and cleaned wheat, and two experiments with barley. In all cases, filtering was by a Hamming window low pass convolution filter with a cut off frequency of 4 Hz on a file of 16,000 points.

| Material | Mean Weight (g) | Variance in Δ Wt for 4 Hz filtered data (Δ Wt²) |
| --- | --- | --- |
| Wheat | 742 | 0.0000144 |
| Wheat | 746 | 0.0000179 |
| Wheat | 740 | 0.0000162 |
| Wheat | 755 | 0.0000160 |
| Wheat | 740 | 0.0000125 |
| Wheat | 736 | 0.0000148 |
| Wheat | 731 | 0.0000157 |
| Wheat | 734 | 0.0000145 |
| Wheat | 738 | 0.0000115 |
| Wheat | 748 | 0.0000167 |
| Cleaned Wheat | 736 | 0.0000110 |
| Cleaned Wheat | 745 | 0.0000157 |
| Cleaned Wheat | 748 | 0.0000106 |
| Cleaned Wheat | 753 | 0.0000105 |
| Cleaned Wheat | 743 | 0.0000116 |
| Cleaned Wheat | 741 | 0.00000972 |
| Cleaned Wheat | 751 | 0.0000123 |
| Cleaned Wheat | 753 | 0.000106 |
| Cleaned Wheat | 748 | 0.0000113 |
| Cleaned Wheat | 741 | 0.0000110 |
| Barley | 586 | 0.000167 |
| Barley | 600 | 0.000162 |

Characterisation of the signals by their variance, after appropriate filtering, gives a robust quantative index that changes with known material changes in the system. It is clear that the mean values of variance of wheat containing chaff and cleaned wheat listed in table 7 differ by about 30%. A t-Test confirms that these apparent differences are highly significant. Likewise, the mean weight of the measuring cell in the experiments with wheat is larger by about 0.7% than the mean weight for cleaned wheat.

In the apparatus shown in FIG. 1, the microprocessor is arranged to determine by reference to the variance in ΔWt, the proportion of one component such as barley for example, to the balance of another component such as wheat for example.

The weight signal sampling rate was 200 Hz and the signal was filtered using a Hamming window low pass convolution filter with a cut off frequency of 4 Hz on a file of 16,000 points for wheat/barley mixtures. The sampling rate and filtering may vary with the types of components present in the flowing material.

The microprocessor contains stored reference or comparative time series information, such as frequency spectra, phase space or other pattern recognition data for the flowing material type under test for reference purposes when carrying out the analysis, or for various types of flowing material.

The foregoing describes the invention and discloses preferred forms thereof. Alterations and modifications as will be apparent to those skilled in the art are intended to be incorporated within the scope hereof.

I claim:
1. A method for determining a characteristic or characteristics of a particulate material, comprising:
   causing the material to flow through a measuring cell of constant volume so as to maintain a substantially constant volume of flowing material in the measuring cell, and
   continuously monitoring the weight of material in the measuring cell and comparing oscillations in the weight of the contents of the measuring cell as the material flows through the measuring cell with comparative information to determine said characteristic(s) of the flowing material.
2. A method according to claim 1 comprising determining the type or constitution, surface characteristics or general flowability of the particulate material by comparing oscillations in the weight of the contents of the measuring cell as the material flows through the measuring cell with stored comparative information.
3. A method according to claim 2 comprising determining the proportions of particles of different sizes or in different size ranges by comparing oscillations in the weight of the contents of the weighing cell with said stored comparative information.
4. A method according to claim 3 comprising determining the proportions of particles of a smaller size relative to a balance of particles of a larger size in the flowing material by comparing oscillations in the weight of the contents of the weighing cell to stored comparative information.
5. A method according to claim 2 comprising determining the proportion of one type of material relative to a balance of one or more other types of material by comparing oscillations in the weight of the contents of the weighing cell to stored comparative information.
6. A method according to any one of claims 1 to 5 including analysing said oscillations in the weight of the contents of the weighing cell to produce frequency spectra or phase space data and comparing this data with stored comparative information of a similar type.
7. Apparatus for determining a characteristic or characteristics of a particulate material, comprising:
   a measuring cell having an inlet by which material may flow into the measuring cell to maintain a substantially constant volume of flowing material in the measuring cell and an outlet for exit of the flowing material,
   weighing means associated with the measuring cell for providing a continuous indication of the weight of the contents of the cell,
   computing means to compare oscillations in the weight of material in the measuring cell with stored comparative information in memory to determine said characteristic(s) of the flowing material.

* * * * *